(12) United States Patent
Drouillard

(10) Patent No.: US 10,278,334 B2
(45) Date of Patent: May 7, 2019

(54) SYSTEMS AND METHODS FOR DELIVERING NUCLEIC ACIDS TO A PLANT

(71) Applicant: GPD Technologies, LLC, Peachtree City, GA (US)

(72) Inventor: Gregory P. Drouillard, Sharpsburg, GA (US)

(73) Assignee: PREMIER CITRUS APZ, LLC, Vero Beach, FL (US)

(*) Notice: Subject to any disclaimer, the term of this patent is extended or adjusted under 35 U.S.C. 154(b) by 0 days.

(21) Appl. No.: 15/468,943

(22) Filed: Mar. 24, 2017

(65) Prior Publication Data

US 2017/0311555 A1    Nov. 2, 2017
US 2018/0098511 A9    Apr. 12, 2018

Related U.S. Application Data

(60) Provisional application No. 62/313,634, filed on Mar. 25, 2016.

(51) Int. Cl.
| | | |
|---|---|---|
| A01N 25/00 | (2006.01) | |
| A01G 7/06 | (2006.01) | |
| C05G 3/02 | (2006.01) | |
| C05F 11/00 | (2006.01) | |
| A01G 7/04 | (2006.01) | |

(52) U.S. Cl.
CPC ............. *A01G 7/06* (2013.01); *A01G 7/04* (2013.01); *A01G 7/045* (2013.01); *A01N 25/00* (2013.01); *C05F 11/00* (2013.01); *C05G 3/02* (2013.01); *Y02P 60/146* (2015.11)

(58) Field of Classification Search
None
See application file for complete search history.

(56) References Cited

U.S. PATENT DOCUMENTS

| | | | | |
|---|---|---|---|---|
| 5,272,072 | A * | 12/1993 | Kaneko | C12N 15/8206 435/460 |
| 5,278,423 | A | 1/1994 | Wangler et al. | |
| 5,660,747 | A | 8/1997 | Drouillard et al. | |
| 5,897,797 | A | 4/1999 | Drouillard et al. | |
| 3,172,328 | A | 1/2001 | Jones et al. | |
| 6,180,914 | B1 | 1/2001 | Jones | |
| 6,508,785 | B1 | 1/2003 | Eppstein | |
| 6,527,716 | B1 | 3/2003 | Eppstein | |
| 7,132,289 | B2 | 11/2006 | Kobayashi et al. | |
| 7,758,561 | B2 | 7/2010 | Eppstein | |
| 9,265,260 | B1 | 2/2016 | Drouillard | |
| 2003/0191458 | A1 | 10/2003 | Diamond | |
| 2005/0210744 | A1 | 9/2005 | Watanabe | |
| 2005/0226975 | A1 | 10/2005 | Drouillard | |
| 2007/0218556 | A1 | 9/2007 | Harris | |
| 2009/0306576 | A1 | 12/2009 | Bragagna | |
| 2010/0298448 | A1 | 11/2010 | Krause et al. | |
| 2011/0277188 | A1 * | 11/2011 | Morawala-Patell | C12N 9/88 800/287 |
| 2013/0047298 | A1 | 2/2013 | Tang | |
| 2013/0052738 | A1 | 2/2013 | Neculaes et al. | |
| 2013/0259954 | A1 | 10/2013 | Masaoka | |
| 2014/0024857 | A1 | 1/2014 | Alves De Souza | |
| 2014/0303546 | A1 | 10/2014 | Badiavas et al. | |
| 2015/0087512 | A1 | 3/2015 | Wang et al. | |

FOREIGN PATENT DOCUMENTS

| | | |
|---|---|---|
| CA | 2276312 | 7/1998 |
| CN | 103202187 | 7/2013 |
| DE | 1273896 | 7/1968 |
| EP | 0483847 | 5/1992 |
| EP | 1225228 | 7/2002 |
| EP | 2681997 | 8/2014 |
| WO | 2010004581 | 1/2010 |
| WO | 2013148677 | 10/2013 |

OTHER PUBLICATIONS

Tang et al.( Efficient delivery of small interfering RNA to plant cells by a nanosecond pulsed laser-induced stress wave for post-transcriptional gene silencing, Plant science (2006), vol. 171, No. 3, pp. 375-381).*
Nakada et al.( Shock wave based biolistic device for DNA and drug delivery, Japanese Journal of Applied Physics (2008), 47(3, Pt. 1), 1522-1526).*
Y.A. Badr et al., Production of fertile transgenic wheat plants by laser micropuncture; The Royal Society of Chemistry and Owner Societies 2005; pp. 803-807.
International Search Report, PCT/US17/51628, filed Sep. 14, 2017.
G. Weber et al., Genetic Manipulation of Plant Cells and Organelles With a Laser Microbeam; Plant Cell, Tissue and Organ Culter 12: 219-222 (1988) Kluwer Academic Publishers, Dordrecht—printed in the Netherlands.
Abstracts of the 2014 Meeting of the Florida State Horticulture Society, Dec. 2014.
CRDF-funded CPD Projects, Commercial Product Delivery Projects Invited to Submit Full Details of Funding Requests, Mar. 30, 2015.
Current CRDF-Funded Research and Delivery Products, Jul. 2015.
Gordon, K.H. et al., "RNAi for insect-proof plants", Nature Biotechnology, vol. 25, No. 11, Nov. 2007, pp. 1231-1232.
Hajeri, S. et al., "Citrus tristeza virus-based RNAi in citrus plants induces gene silencing in Diaphorina citri, a phloem-sap sucking insect vector of citrus greening disease (Huanglongbing)", Journal of Biotechnology, vol. 176, 2014, pp. 42-49.
International Search Report and Written Opinion, PCT application No. PCT/US15/65123, dated Jul. 29, 2016.

(Continued)

*Primary Examiner* — Alton Nathaniel Pryor
(74) *Attorney, Agent, or Firm* — Fish IP Law, LLP

(57) ABSTRACT

A method of delivering at least one nucleic acid to a plant, comprising: applying a light energy to a surface of the plant to create a pore; and applying at least one nucleic acid to the pore, wherein the at least one nucleic acid comprises RNA, wherein the at least one nucleic acid comprises at least one of a RNA interference (RNAi), an antisense RNA (asRNA), a micro RNA (miRNA), a small interfering RNA (siRNA), a double-stranded RNA (dsRNA), a non-coding RNA (ncRNA), mitochondrial RNA (mtDNA), and combinations thereof.

21 Claims, 6 Drawing Sheets

(56) References Cited

OTHER PUBLICATIONS

Office Action, U.S. Appl. No. 14/995,120, dated Sep. 19, 2017.
Office Action, U.S. Appl. No. 14/551,902, dated May 5, 2015.
Younis, A. et al., "RNA Interference (RNAi) Induced Gene Silencing: A Promising Approach of Hi-Tech Plant Breeding", International Journal of Biological Sciences, vol. 10, 2014, pp. 1150-1158.
Office Action, U.S. Appl. No. 15/468,943, dated Oct. 3, 2017.
Etxeberria, Ed et al, The Anatomy of a Laser Label, Florida State Horticulture Society, 2009, 122:347-349.
Sood, Preeti et al, Laser Etching: A Novel Technology to Label Florida Grapefruit, HortTechnology, Jul.-Sep. 2009 19 (3), pp. 504-510.
Office Action, U.S. Appl. No. 14/965,850, dated Mar. 7, 2018.
Jerry Newlin, Minutes of Board of Directors Meeting, Citrus Research and Development Foundation, Inc., Mar. 25, 2014, Lake Alfred, Florida.
Office Action, U.S. Appl. No. 14/995,120, Dated Mar. 29, 2018.
Canadian Office Action dated Sep. 28, 2018 for Canadian Application No. 3,008,016 in the name of Premier Citrus APZ, LLC entitled Systems And Methods For Using Light Energy To Facilitate Penetration Of Substances In Plants (11 pages).

\* cited by examiner

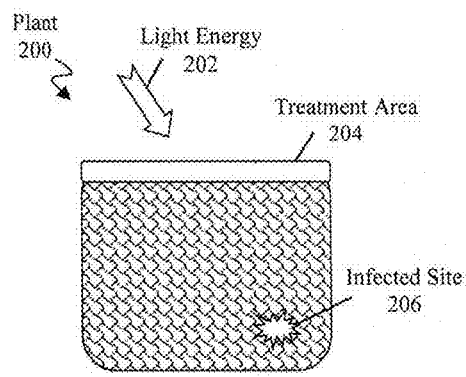
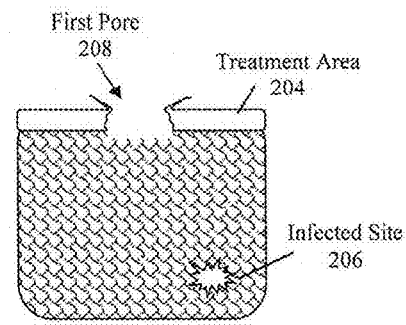
Figure 2A
Figure 2B
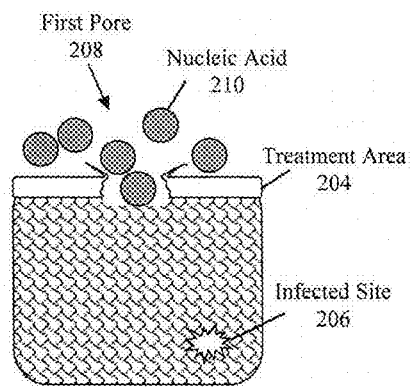
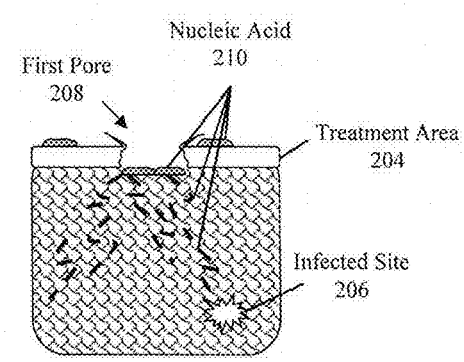
Figure 2C
Figure 2D
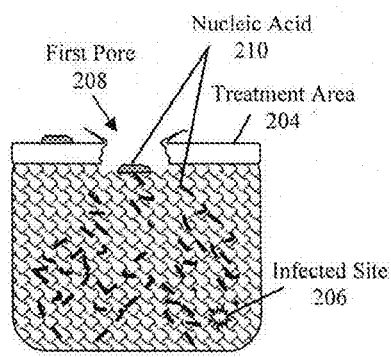
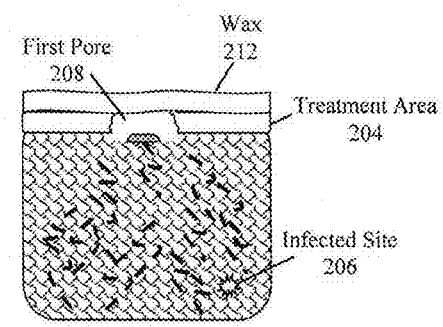
Figure 2E
Figure 2F

SYSTEMS AND METHODS FOR DELIVERING NUCLEIC ACIDS TO A PLANT

CROSS REFERENCE TO RELATED APPLICATIONS

This application claims the benefit of U.S. Provisional Application No. 62/313,634 filed on Mar. 25, 2016, entitled "Systems and Methods for Delivering Nucleic Acids to a Plant", the contents of which are incorporated herein by reference as though set forth in their entirety.

BACKGROUND

This invention is directed to devices and methods for delivering nucleic acids into a plant using a laser.

The background description includes information that may be useful in understanding the present invention. It is not an admission that any of the information provided herein is prior art or relevant to the presently claimed invention, or that any publication specifically or implicitly referenced is prior art.

Plant pathogens pose numerous challenges to the plant industry. One of the most serious challenges involves controlling pathogens to prevent significant plant losses. For example, Huanglongbing (hereinafter referred to as "HLB") or citrus greening disease has led to a loss of many citrus trees. Consequently, HLB may be very damaging to the crop yield in large scale operations.

Some have contemplated using RNA interference (hereinafter referred to as "RNAi") to improve the characteristics of a plant. For example, Younis et al., contemplates RNAi as a tool to engineer pathogen resistant plants, insect/pest resistant plants, and improved quality plants. Adnan Younis et al., RNA Interference (RNAi) Induced Gene Silencing: A Promising Approach of Hi-Tech Plant Breeding, International Journal of Biological Sciences 2014, Vol. 10: 1150-1158. Others have contemplated similar uses of RNAi in plants, including Karl H. J. Gordon et al., RNAi for insect-proof plants, Nature Biotechnology 2007, Vol. 10: 11, Hajeri et al., Citrus tristeza virus-based RNAi in citrus plants induces gene silencing in *Diaphorina citri*, a phloem-sap sucking insect vector of citrus greening disease (Huanglongbing), Journal of Biotechnology 176 (2014) 42-49, and Wie Tang et al., Efficient delivery of small interfering RNA to plant cells by a nanosecond pulsed laser-induced stress wave for posttranscriptional gene silencing, Plant Science 171 (2006) 375-381. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Nucleic acids, and more specifically RNAi, may be used to enhance a plant as briefly described above. Some have contemplated delivering RNA into a plant to control pathogen and/or pest control damage. For example, Tang (US 2013/0047298) contemplates spraying or brushing the surface of a plant with a double-stranded RNA (hereinafter referred to as "dsRNA") to promote penetration of dsRNA into plant cells. Although spraying or brushing is less invasive than other delivery methods, it appears that the uptake of RNA by spraying or brushing may be compromised due to the relatively low permeability of the outer layer of some plants.

Thus, there is still a need in the art for improving uptake of nucleic acids (e.g., RNAi) in plants.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later. It is to be understood that both the following general description and the following detailed description are exemplary and explanatory only and are not restrictive.

In accordance with the embodiments disclosed herein, the present disclosure is directed to an apparatus, systems, and methods in which light energy may be used to enhance uptake of nucleic acids in plants. As used herein, the term "plant" means any type of plant life, including a tree, vines, forage, perennial crops, row crops, bush crops, an ornamental plant, annual plants, and grasses. A light energy may be applied to a surface of a plant to create a pore, and the nucleic acid is applied to the pore. It should be appreciated that a pore may be a rupture, an ablation, a disruption or a minor incision. Thus, genetic activity within the plant may be efficiently and effectively modified.

In one embodiment, a plant having a disease may be treated. For example, light energy may be applied to a treatment area to create a pore, and nucleic acid may be applied to the pore in an amount effective to treat a disease in an infected site. Contemplated diseases are typically systemic in nature, which means that a pathogen occurs within plant tissue. However, it is also contemplated that surface diseases (e.g., citrus canker) may also be treated. Thus, instead of applying excessive dosages of a nucleic acid via a spray to treat surface diseases, it is contemplated that the dosage amount of the nucleic acid may be greatly reduced by feeding the nucleic acid to a pore created by the light energy. It should be appreciated that treating a plant does not require a complete cure of the plant from the disease, but may also include a reduction in the disease state or a reduction in a symptom of the disease.

In one embodiment, the step of applying a light energy includes creating a pore pattern. The pore pattern may be a single pore or a plurality of pores, wherein the plurality of pores may be arranged in a single line, a plurality of lines, a continuously bending line (e.g., swirls, random curves, etc.), a plurality of continuous bending lines, and combinations thereof. It is contemplated that the pore pattern may influence the amount of the first dosage of the nucleic acid that may be required to be effective to induce a therapeutic response. Furthermore, the first pore may have a diameter of approximately 100 to 300 μm. It should be appreciated that the various pore depths, widths, lengths, surface areas, and patterns may be used to promote a therapeutic response in a minimally invasive manner. It should be understood that the terms "pore," "first pore," "second pore", or the like may refer to single pore or a plurality or grouping of pores.

In one embodiment, the step of applying a light energy may be before the step of applying the first dosage. However, it should be appreciated that the reverse order may also be performed to treat plant. A predetermined time may also be used to regulate the performance of such steps to ensure effective uptake of the nucleic acid into the plant via the first indentation. For example, the step of applying a light energy and the step of applying a first dosage may be performed in less than an hour, less than 30 minutes, or even less than 1 minute from one another.

As briefly mentioned above, the infected site may be in a phloem. In such embodiment, suitable treatment areas include a surface of at least one of a leaf, a stem, and a bark of the plant. For example, a plant can be a citrus tree having HLB. The citrus tree having HLB has an infected site of the phloem. To treat the citrus tree, light energy can be applied to create a first pore or pores on a treatment area, which can include at least one of a leaf, a steam and a bark. Once the pore is created, a first dosage of a nucleic acid may be applied to the treatment area in an amount effective to induce a therapeutic response (e.g., reduce a symptom of HLB). It should be appreciated that the first pore may comprise a rupture of a cuticle on the leaf to allow introduction of the nucleic acid.

While the embodiments described above have discussed a light energy creating a first pore, it is contemplated that the step of applying the light energy to the treatment area may include creating a second pore. With a second pore, the first dosage of the nucleic acid may be beneficially received by the first and second pores. Thus, additional pores may be contemplated so long as the amount of pores created is minimally invasive to prevent or reduce damage to the plant.

In order to reduce the risk of damage to the plant, in one embodiment, wax may be applied to the treatment area in an amount effective to seal the first pore after the steps of applying the light energy to the treatment area and applying the first dosage of a nucleic acid to the treatment area are complete. As a further step of precaution an antifungal spray may be applied to the treatment area.

The treatment area and the infected site may be in distinct plant systems within the plant. For example, the treatment area may be in the dermal system of the plant (e.g., cuticle, cork) while the infected site may be in the vascular system of the plant (e.g., phloem). In addition, as briefly discussed above, the treatment area and infected site may be distal. As used herein, "distal" means situated away from. In some instances, distal may refer to a physical distance between the treatment area and the infected area, for example, a distance of between 0.01 cm to 100 cm, more preferably, between 0.05 cm to 50 cm, and most preferably, between 0.1 cm to 25 cm. In other instances, distal may refer to a distance between treatment area and infected site in terms of a systemic pathway. For example, the treatment area and the infected site are distal by one to two layers of a plant epidermis or one to two layers of bark tissues. In addition, distal could refer to a systemic distance that crosses multiple systems (e.g., dermal system, vascular system, ground system). Moreover, distal could refer to locations on different branches and/or leaves of a plant.

In another embodiment, a first nucleic acid may be delivered to a first site in a plant. In such embodiment, a light energy may be applied to a second site located on a plant surface. The first site (e.g., phloem, xylem) and the second site (e.g., cuticle, cork) may be different in kind. In other words, the first site and the second site may be different plant systems (e.g., dermal system, vascular system) or different plant tissues. A first dosage of the first nucleic acid may be applied to the second site in an amount effective to promote uptake of the first nucleic acid and delivery to the first site via the second pore.

The plant may include a tree, row crop, a bush crop, and an ornamental plant. Furthermore, as a precautionary measure, a wax may be applied to the second site in an amount effective to seal the second pore after the steps of applying the light energy to the second site and applying the first dosage of the nucleic acid to the second site.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

FIGS. 2A-2F are perspective views of an embodiment showing deliver of the first nucleic acid from a treatment area to an infected site.

DETAILED DESCRIPTION OF THE ILLUSTRATIVE EMBODIMENTS

Figure 1:
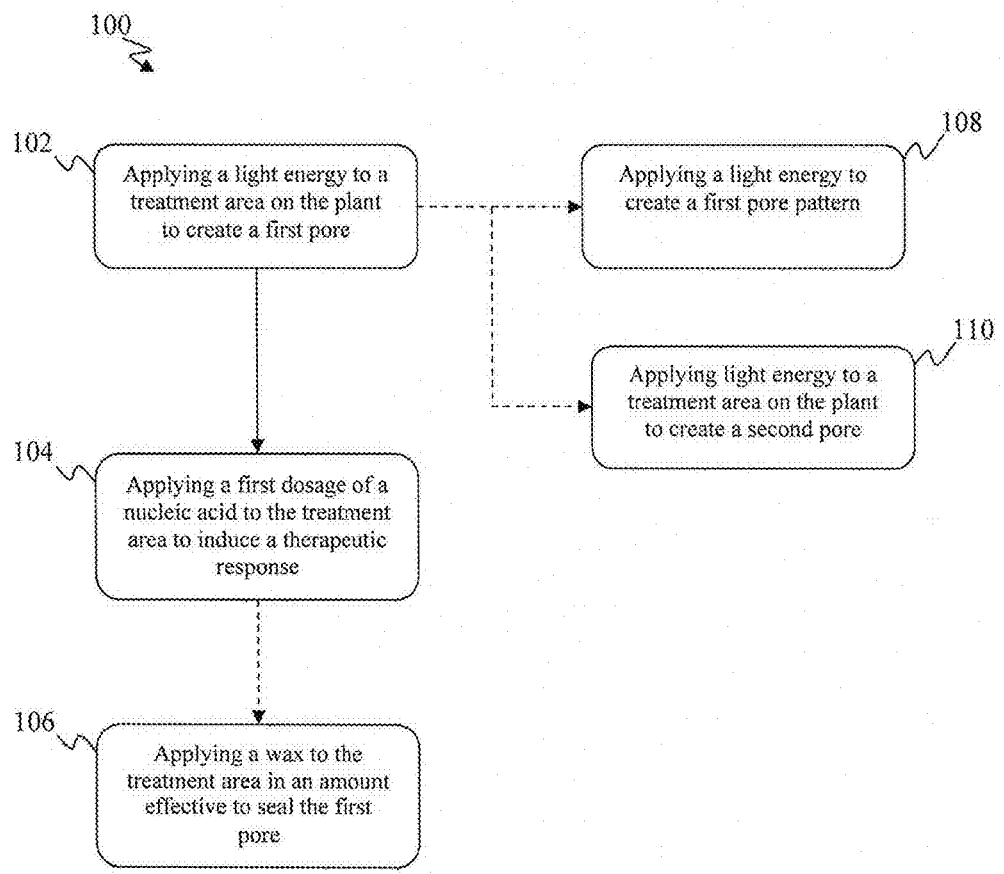
FIG. 1 is a flow diagram of a method of treating a plant having a disease in an infected site of the plant.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.01-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form in order to facilitate describing these embodiments.

It has been discovered that light energy may be used to enhance the penetration of a nucleic acid in plants. This may be accomplished by applying a light energy to a first portion of a plant to create an indentation. Once the indentation is created, a first dosage of a substance may be applied to the plant. It should be appreciated that at least a portion of the first dosage may penetrate the plant via the indentation.

FIG. 1 shows a schematic of a method 100 for treating a plant having an infected site. The method 100 may comprises a step 102 of applying a light energy to a treatment area on the plant to create a first pore. Typically, the treatment area may be distal from the infected site. In another step 104, a first dosage of a nucleic acid may be applied to the treatment area in an amount effective to induce a therapeutic response in the infected site. Suitable therapeutic responses may include, but are not limited to, a complete cure of a disease causing the infected area, a reduction in the infected area, a reduction in a symptom of the disease causing the infected area, a health stimulant, and combinations thereof.

In preferred embodiments, step 102 of applying the light energy to the treatment area may occur prior to step 104 of applying the first dosage of the nucleic acid. However, it is contemplated that the reverse order may be performed to treat a plant whereby step 104 occurs prior to step 102. Regardless of the order in steps 102 and 104, a predetermined time may be used to determine when each step may be completed with respect to one another. For example, step 102 and step 104 may be completed within less than 1 hour, more preferably less than 30 minutes, and most preferably within 1 minute of one another. Therefore, uptake of the nucleic acid via the first indentation may be enhanced by performing steps 102 and 104 within the predetermined time.

It is further contemplated that the parameters of the first pore (e.g., size, shape, depth, pattern, etc.) may influence the therapeutic response in the infected area. An additional step 108 of applying a light energy may include creating a pore pattern. Suitable pore patterns may be as simple as one pore or a line of pores. Pore patterns may be more complex and may include a plurality of pores arranged in lines, continuously curved lines, or a combination thereof. It should be appreciated that pore patterns may influence the uptake of the nucleic into the plant by providing different dimensional shapes and areas for absorption. In one embodiment, the method 100 may include an additional step 110 of applying the light energy to create a second pore, or any number of additional pores.

The method 100 may also include an additional step 106 of applying a wax to the treatment area in an amount effective to seal the first pore and any additional pores. In one embodiment, the step of applying the wax may be performed after the steps of applying the light energy to the treatment area and applying the first dosage of a nucleic acid to the treatment area. In this fashion, the first pore may be sealed from the outside environment to prevent harmful contaminants from accessing the plant through the first pore. In addition, the wax may reduce the amount of perspiration of the substance to help its absorption into the plant.

FIGS. 2A-2F shows a cross section of a plant 200, which has an infected site 206. As discussed above, plant 200 may comprise any type of plant life, including a tree, vines, forage, perennial crops, row crops, bush crops, an ornamental plant, annual plants, and grasses. Thus, it should be noted that the methods disclosed herein may be applied to all different plant types to improve the delivery of a nucleic acid into the plant. In one example, plant 200 is a citrus tree.

Infected site 206 may have an area affected by various known diseases/pathogens. However, it is contemplated that a plant may have a plurality of infected sites. Contemplated diseases are typically systemic in nature, which means that the pathogen occurs within plant tissue. Consequently, the treatment of such diseases is difficult to control using conventional surface treatments. For example, contemplated diseases include HLB, Citrus Tristeza Virus (CTV), Citrus Variegated Chlorosis (CVC), Laurel wilt disease, Fusarium wilt, Phytoplasmas, Zebra chip disease, bacterial kiwifruit vine disease, Chestnut blight, Oak wilt, Fusarium wilt and Pierce's disease.

Infected site 206 may be an area in a plant affected by a disease, such as HLB, Citrus Tristeza Virus (CTV), Citrus Variegated Chlorosis (CVC) Laurel wilt disease, Fusarium wilt, Phytoplasmas, Zebra chip disease, bacterial kiwifruit vine disease, Chestnut blight, Oak wilt, Fusarium wilt, and Pierce's disease. While FIG. 2A shows infected site 206 within plant 200, it is contemplated that infected site 206 may reside on the outside surface of plant 200, such as in the case of citrus canker. It should also be noted that while the methods disclosed thus far relate to treating diseased plants, the methods herein may also be applied to healthy plants for preventive care or to promote overall health (e.g., fertilizer application).

FIG. 2A shows a light energy 202 may be applied to a treatment area 204 of plant 200. Treatment area 204 is typically on a surface of plant 200. However, it is contemplated that treatment area 204 may also be within plant 200 (i.e., beyond the outer epidermis). Treatment area 204 may be a region of a plant or a specific organ of a plant (e.g., leaf, bark, stem, etc.). In addition, treatment area 204 may comprise a targeted coverage area of a plant. For example, treatment area 204 may comprise less than 25% of the surface area of the plant (e.g., leaf, stem, trunk, etc.), and more preferably less than 20% of the surface area of a plant.

Treatment area 204 is typically distal from infected site 206. For example, treatment area 204 may be a surface of at least one of a leaf, a stem, and a bark, while the infected site is in a phloem of plant 200. In particular, treatment area 204 may be in the dermal system of plant 200 while the infected site 206 may be in the vascular system of plant 200. Therefore, it is contemplated that the treatment area and the infected site are in distinct plant systems (e.g., dermis, vascular, ground).

Light energy 202 may be used to create a first pore 208 as shown in FIG. 2B. Co-invented U.S. Pat. Nos. 5,660,747 and 5,897,797, and U.S. Pat. Pub. 2005/0226975 describe various techniques for etching the skin of produce using energy from a $CO_2$ laser. It is contemplated that the present inventive subject manner may employ some of the techniques in these references, or modifications thereof, in combination with suitable operational parameters, to accomplish the objectives of the present inventive subject matter. For example, light energy 202 may comprise a $CO_2$ laser that may be configured with suitable parameters (e.g., size/diameter, quality, spatial intensity distribution, divergence, wavelength, etc.) that are sufficient to produce a desired pore in a particular treatment surface (e.g., leaf). In some embodiments, suitable parameters for light energy 202 (e.g., a laser) may include a wavelength having about 10 micrometers (e.g., 10.6 micrometers) and a power output range between 20-90% at 30-2000 microseconds. It is contemplated that the power output of light energy 202 may range from 10-100 watts. It should be appreciated that the suitable parameters may be adjusted in real-time to accommodate various environmental factors that could affect light energy 202.

As treatment area 204 may comprise different parts of plant 200 (e.g., leaf and bark), it is contemplated that different parameters of light energy 202 may be used for different parts of plant 200. For example, light energy 202 applied to a bark to create a pore typically requires more power and dwell than light energy 202 applied to a leaf to create a pore. Suitable power settings for applying light energy 202 to a bark may be in the range of 80-90% power at a dwell 1200-2000 microseconds depending on the age of plant 200. On the other hand, grasses would typically require less power in the range of 20-50% power at a dwell of 30-120 microseconds.

Other contemplated parameters for light energy 202 include jump speeds, marking speeds, marking intensities, pulse frequencies, and the like. Jump speeds may range from 1 to 3000 mm/s, and more typically between 1000-2000 mm/s. Marking speeds may range from 100 to 3000 mm/s, and more typically from 1000-2000 mm/s. Marking intensity may range from 20-100%, and more typically between 30-70%. Pulse Frequency may range from 15 to 20000 Hz, and more typically between 1000-20000 Hz. It should be appreciated that the jump speeds, marking speeds, marking intensities, and pulse frequencies may be applied to all areas of plant 200, including the leaves, branches, stems, bark.

Additionally, it is contemplated that light energy 202 may be generated using a 400 mm output lens, which provides a scan window of approximately 14 inches by 14 inches without changing the beam characteristics and energy. The scan window is the area that may be lased by light energy 202. For example, it is contemplated that such output lens provides an optimum focal distance of 15 inches and an effective depth of focus of 9 inches. It should be appreciated that the focal point and depth of focus may be changed based on the size of the output lens used. For example, a 200 mm lens provides a focal point of 7 inches and a depth of focus of 4 inches, and a 800 mm lens provides a focal point of 23 inches and a depth of focus of 15 inches. Thus, it should be appreciated that a "scribing" laser or continuous wave laser is contemplated, which may be air cooled and designed for the outdoor environment.

Furthermore, it should be noted that a galvanometer may be used to control a scribing path of the light energy 102. Typically, the galvanometer is placed behind the laser output lens, such that light energy 102 travels to the galvanometer before the laser output lens. Furthermore, it should be appreciated that more than one galvanometer may be used to control the direction of light energy 102 in two directions (e.g., x and y directions).

As discussed above, suitable parameters for light energy 202 may vary depending on environmental factors, among other things. To better operate a real-time system that adjusts light energy 202, it is contemplated that a control system (e.g., a feedback loop) having sensors are integrated with light energy 202. The sensors may be used to detect various parameters affecting the application of light energy 202, such as the different parts of plant 200 (e.g., bark vs. leaf), weather, age of plant 200, depth and size of first pore 208, and the distance from the light energy source and treatment area 204. Upon obtaining sensor data on various parameters, the control system may adjust light energy 202 to create a pore. For example, a sensor may detect that treatment area 204 is part of the bark of plant 200 and adjust the power settings of light energy 202 to create a pore, and at a subsequent point in time the sensor may detect that treatment area 204 is on the surface of grass and adjust the power settings by reducing power of light energy 202 to create a pore. In another example, light energy 202 may have a default setting (e.g., power setting to create a pore on a leaf of plant 200) and, upon sensing another part (e.g., stem, bark) of plant 100, control system may adjust light energy 202 to create a pore before returning to the default setting. In yet another example, a sensor may be integrated within light energy 202 to determine whether first pore 208 has reached a pre-determined tissue layer.

In contemplated embodiments, light energy 202 may be applied having the light energy source in contact with treatment area 204. However, in other more typical embodiments, light energy 202 may be applied having the light energy source at a distance from treatment area 204. For example, the light energy source may be between 4 to 14 inches (e.g., 7 inches) from treatment area 204. In another example, light energy 202 may comprise a $CO_2$ laser and treatment area 204 may be on a surface of a leaf whereby the distance between the $CO_2$ laser and the leaf is between 4 to 14 inches, and more preferably, 5 to 8 inches.

First pore 208 may be removed or disrupted portion of treatment area 204. In contemplated embodiments, first pore 208 may comprise an opening through the treatment area 104. In other words, first pore 208 may extend through treatment area 204 to expose a surface underneath treatment area 204. For example, first pore 208 may be a rupture, ablation, or disruption of a cuticle on the leaf. It should be appreciated that first pore 208 is intended to be minimally invasive to the plant. Therefore, typical diameters for first pore 208 may be approximately between 100 and 300 μm, and typically have a depth of approximately 50 μm. It should be noted that first pore 208 may have a greater or lesser depth, but the depth should generally not exceed 75 μm as it may destroy too many cells.

While first pore 208 may extend through treatment area 204, it is also contemplated that first pore 208 may extend partially through treatment area 204. In other words, first pore 208 need not be a complete breach through treatment area 204 (e.g., the depth of first pore 208 does not extend into the entire thickness of the cuticle). On the other hand, it is also contemplated that first pore 208 may extend through various layers past treatment area 204. Preferably, first pore 208 may be configured to achieve maximum uptake of the nucleic acid while minimizing harm to the plant.

Once first pore 308 is created, a first dosage of a nucleic acid 310 may be applied to treatment area 204 as shown in FIG. 2C. Nucleic acid 210 typically promotes the overall health or treatment of plant 200. It is contemplated that nucleic acid 210 may comprise RNA. Suitable RNA for nucleic acid 210 may include at least one of a RNA interference (RNAi), an antisense RNA (asRNA), a micro RNA (miRNA), a small interfering RNA (siRNA), a double-stranded RNA (dsRNA), a non-coding RNA (ncRNA), and mitochondrial RNA. For example, nucleic acid 210 may be RNAi that at least one of (i) modifies a gene expression to increase resistance to a pathogen in the plant (e.g., interfere with the metabolism or development process, affect the development of an insect (e.g., citrus psyllid) that feeds on the plant (wings, gut, offspring, etc.)), (ii) suppresses a virus-based vector in the plant, and (iii) modifies a gene expression to obtain a favorable trait in the plant (e.g., color, flavor, reduced degradation, reduced abiotic stress, etc.). Thus, it is contemplated that RNAi may be applied via foliar application with enhanced uptake due to the pores created by the light energy.

It is also contemplated that nucleic acid 210 may comprises at least one of DNA and a nucleic acid analogue. Nucleic acid 210 may also comprise a tag for detection to determine whether there was uptake of nucleic acid 210 into plant 200. Moreover, nucleic acid 210 may also comprise a pharmaceutical tag to enhance or complement the action of the nucleic acid 210. Nucleic acid 210 may have any number of base or base pairs. For example, nucleic acid 110 may have 1-10, 8-20, 12-30, 25-50, 40-100, 100-1,000, 1,000-10,000, and 10,000-1,000,000 base pairs.

Nucleic acid 210 may have various suitable structures and characteristics. For example, nucleic acid 210 may be single or double stranded and circular or linear. Nucleic acid 210 may be coding or noncoding (e.g., noncoding DNA, non-coding RNA). Where protein is encoded by nucleic acid 210, it is contemplated that such proteins are under the control of the regulatory mechanisms specific to plant 210 or a disease or pathogen or to neither. Moreover, nucleic acid 210 may comprise at least one of yeast artificial chromosomes (YACs) and a phagemid plasmid.

Nucleic acid 210 may be with or without sequences that support replication. It is also contemplated that the sequences may be from non-plants (e.g., animal, bacteria, yeast, fungi, etc.). The sequences may also be chimeric (e.g., part animal and part plant, part plant and part bacteria, etc.).

First dosage of nucleic acid 210 will depend on the type of nucleic acid 210 being applied. For example, it is contemplated that nucleic acid 210 may have a concentration of 0.1-1 pmol, 1-10 pmol, 10 pmol-1 nmol, 1-10 nmol, 10 nmol-1 μmol, 1-10 μmol, 10 μmol-1 mmol, and even higher. Thus, depending on the size of nucleic acid 210 it is contemplated that first dosage comprises 0.1-1 pmol/ml, 1-10 pmol/ml, 10 pmol/ml-1 nmol/ml, 1-10 nmol/ml, 10 nmol/ml-1 μmol/ml, 1-10 μmol/ml, 10 μmol/ml-1 mmol/ml, and even higher. First dosage of nucleic acid 210 may be buffered or non-buffered solution.

First dosage of nucleic acid 210 may comprise additional components. It is contemplated that first dosage of nucleic acid 210 may comprise at least one of stabilizers, surfactants, and a nucleic acid degradation inhibitor (e.g., DNAse inhibitor, RNAse inhibitor). Thus, first dosage of nucleic acid 210 may be co-administered with other compounds. It is contemplated that first dosage of nucleic acid 210 may comprise counter ions if, for example, at neutral pH.

Nucleic acid 210 may be applied to first pore 208 using various methods, including spraying, dusting, sprinkling, brushing, smearing and drenching. Application of the first dosage may also be accomplished by introducing nucleic acid 210 into an irrigation system (e.g., sprinkler system) that delivers water to plant 200. It should be appreciated that first dosage of nucleic acid 210 may comprise a surfactant to increase absorption of nucleic acid 210 in plant 200. Using these application techniques, at least some of nucleic acid 210 enters first pore 208. It is also contemplated that a more targeted application technique may be used to focus the application of nucleic acid 210 onto the area of first pore 208.

In yet other embodiments, nucleic acid 210 may produce a harmful response to plant 200 to thereby kill and eliminate plant 200. In this manner, the methods and devices disclosed herein may be used to selectively remove certain plants from a crop, such as to remove weeds, infected plants, older plants, etc. In such embodiments, first pore 208 may be configured to optimize uptake without concern of being minimally invasive.

It is further contemplated that nucleic acid 210 is packaged into a variety of lipid soluble nano-particles. These nano-particles should provide for higher retention rates and for improved cuticle penetration. When combined with the use of light energy to create a pore for nucleic acid 210, penetration of nano-particles (or nucleic acids in solution) may be exceptionally enhanced.

Typically, nucleic acid 210 is better absorbed through first pore 208 as shown in FIG. 2D. Among the various reasons for the better absorption, it should be noted that nucleic acid 210 within first pore 208 has a more direct path into plant 200 as opposed to nucleic acid 210 that is on the outer layer (i.e., outer surface of treatment area 204) of plant 200. It is preferred that the first dosage of nucleic acid 210 applied to treatment area 204 is in an amount effective to induce a response (e.g., therapeutic response, biological response) in infected site 206.

Plant 200 may respond in various manners. For example, plant 200 may have a therapeutic response or biological that comprises a reduction in the infected site 206 as shown in FIG. 2E. In another example, the therapeutic response may comprise at least one of reducing a symptom of a pathogen, reducing a cause of the disease, and completely curing a disease. It is contemplated that nucleic acid 210 may be RNAi and the therapeutic response comprises at least one of (i) modifying a gene expression to increase resistance to a pathogen in plant 200 (e.g., interfere with the metabolism or development process, affect the development of an insect (e.g., citrus psyllid) that feeds on the plant (wings, gut, offspring, etc.)), (ii) suppressing a virus-based vector in plant 200, and (iii) modifying a gene expression to obtain a favorable trait in plant 200 (e.g., color, flavor, reduced degradation, reduced abiotic stress, etc.). Thus, it is contemplated that nucleic acid 210 may affect (i) one or more components of plant 200, (ii) one or more components of a symbiotic organism, and (iii) one or more components of a pathogen.

After creating first pore 208 and applying nucleic acid 210, a wax 212 may be applied to treatment area 204 as shown in FIG. 2F. It should be appreciated that wax 212 has several benefits, including preventing pathogen or other harmful contaminants from entering first pore 208, reducing water loss, and reducing perspiration of nucleic acid 210 from first pore 208. Thus, water loss will be mainly localized and should not affect the overall tree water relations.

Figure 3A:
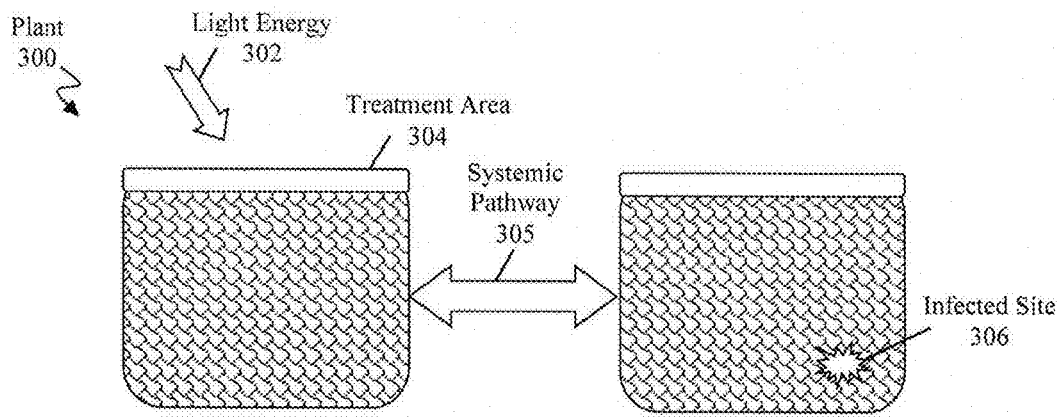
FIGS. 3A-3F are perspective views of an embodiment showing deliver of a first nucleic acid from a treatment area to an infected site separated by a systemic pathway.
Figure 3B:
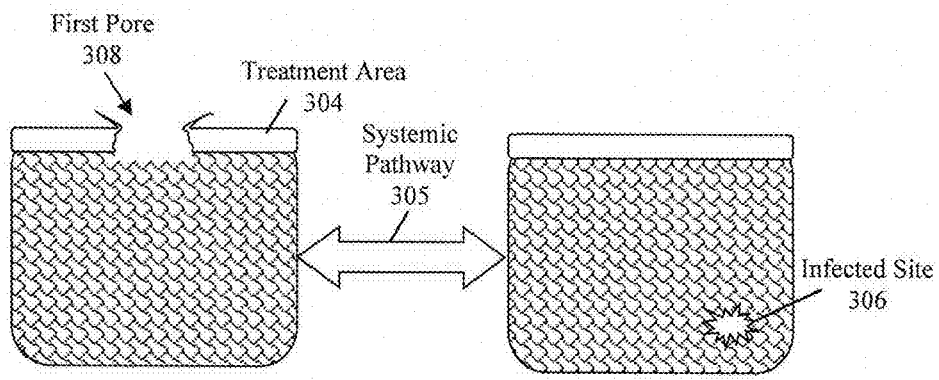
Figure 3C:
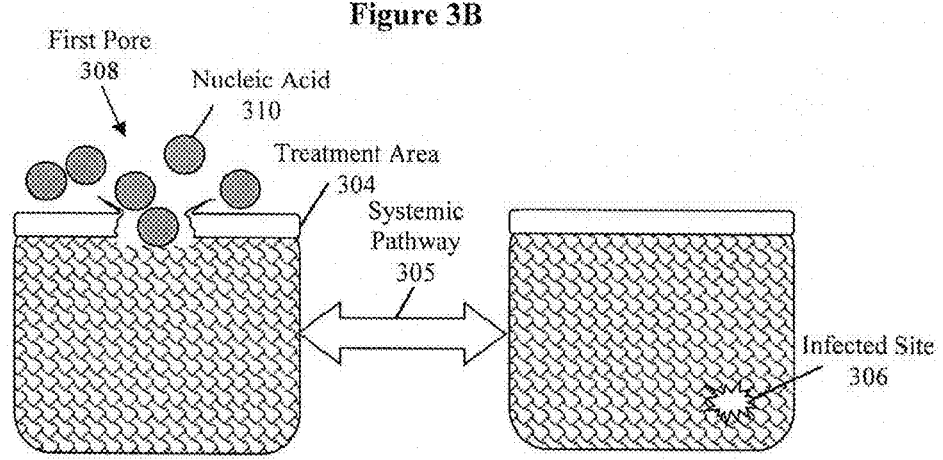

FIGS. 3A-3F shows a cross section of a plant 300, which has an infected site 306 that is distally located from a treatment area 304 across a systemic pathway 305. For example, treatment area 304 could be located on a first leaf and infected site 306 could be located on a second leaf, wherein the first leaf and separate leaf are located on different stems and/or branches. Light energy 302 may be applied to treatment area 304 to create first pore 308 as shown in FIGS. 3A-3B. Once first pore 308 is created, a first dosage of nucleic acid 310 may be applied to treatment area 304 as shown in FIG. 3C. As discussed above, nucleic acid 310 may be applied using various application methods and may further comprise a surfactant to increase absorption.

Figure 3D:
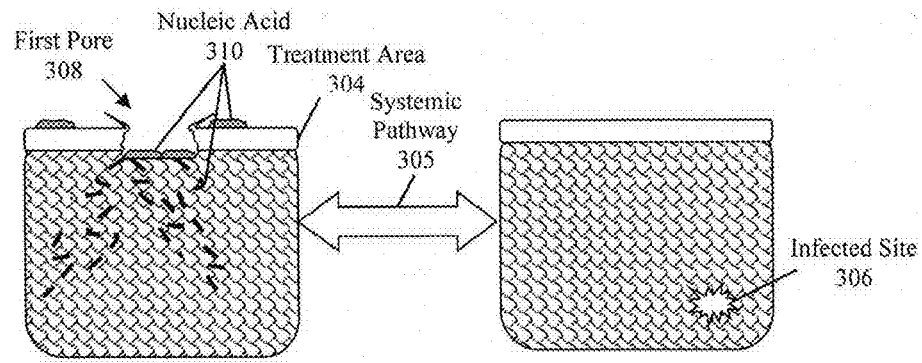

Nucleic acid 310 may absorbed by plant 300 through first pore 308 as shown in FIG. 3D. While nucleic acid 310 has been introduced within plant 300, it should be noted that in some circumstances the infected site 306 is distal from treatment area 304, such that nucleic acid 310 is not immediately in contact with infected site 306 and is separated by a systemic pathway. Thus, first dosage of nucleic acid 310 and first pore 308 may be configured (e.g., the quantity of first dosage, number of applications of dosage, size and depth of first pore 308, percentage of coverage of first pore 308, etc.) to allow for sufficient uptake and delivery of the nucleic acid 310 to the infected site 306 to achieve a therapeutic response at the infected site 306.

Figure 3E:
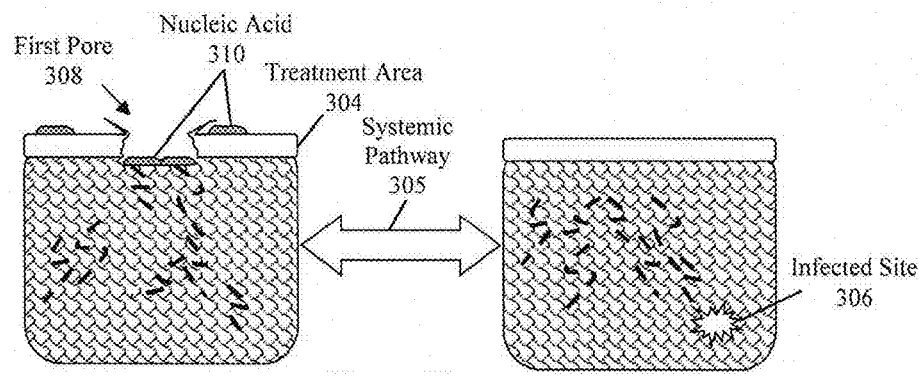
Figure 3F:
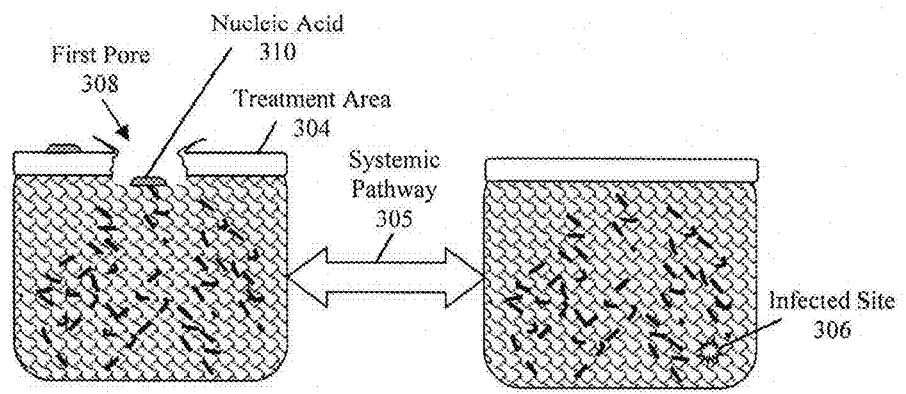
Figure 4A:
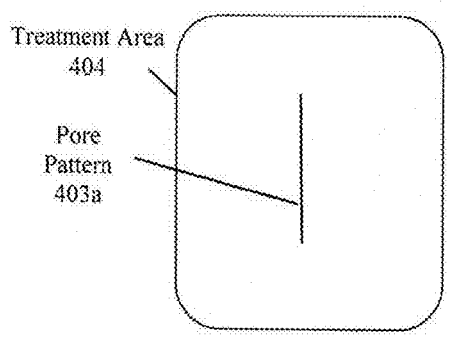
FIGS. 4A-4D illustrates various embodiments of pore patterns.
Figure 4B:
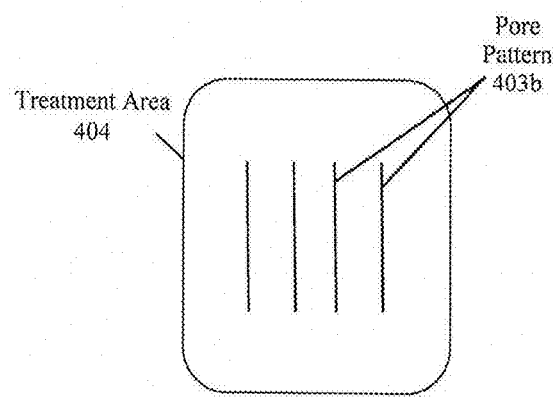
Figure 4C:
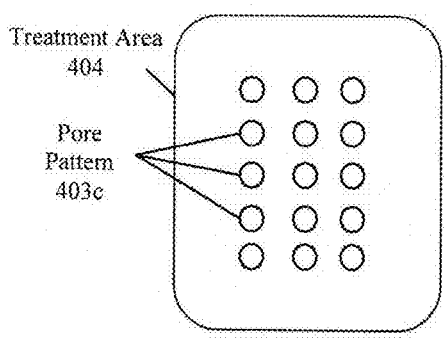
Figure 4D:
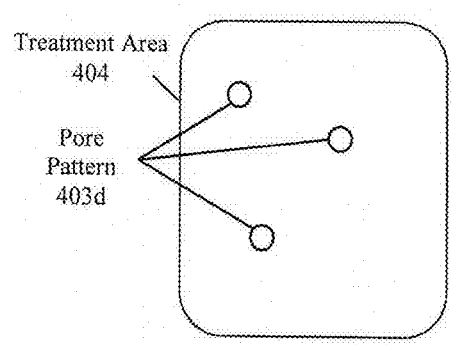

It is contemplated that nucleic acid 310 may travel through a systemic pathway 305 to arrive at infected site 306 as shown in FIG. 3E. While nucleic acid 310 is shown to be present in the area immediately adjacent to first pore 308, it is contemplated that nucleic acid 310 does not have an effect (e.g., therapeutic or biological response) until it travels through systemic pathway 305. FIG. 3F shows first pore 308 and nucleic acid 310 may be sufficient to induce a therapeutic response, such as reducing the area of infected site 306. However, it is also contemplated that nucleic acid 310 remains localized in the area adjacent to treatment area 304 (e.g., within the same leaf, or within the leaves on a single branch, etc.).

It is contemplated that at least 20%, 30%, 50%, 75%, 90% of nucleic acid 310 may be absorbed by at least one of the phloem and the xylem in plant 300. In some embodiments, nucleic acid 310 may be localized in the phloem adjacent to treatment area 304 and not travel to the roots. However, it is also contemplated that nucleic acid 310 may be absorbed by the phloem and/or xylem to thereby travel through the vascular system of plant 300. Regardless of the mode of transport, it should be noted that limited application of nucleic acid 310 may generate an effect throughout 1-5%, 5-15%, 15-35%, 35-60%, 60-90%, and 90-100% of the plant within 1 hour, 2 hours, 5 hours, 10 hours, 18 hours, 1 day, or 2 days.

As discussed above, a treatment area may have more than one pore and may comprise a pore pattern. FIGS. 4A-4D show a treatment area 404 that may have various pore patterns 403a-d. For example, pattern 403a is a single solid line, pattern 403b comprises multiple solid lines, pattern 404c comprises a plurality of circular dots equally distanced from one another, and pattern 404d comprises a plurality of randomly spaced dots. However, while creating a plurality of pores provides increased sites for direct introduction of the substance into the plant, it is generally preferred that not more than 25% of the surface area of the plant be covered with pores to avoid permanent damage to the plant. In some applications, more than 25% of the surface area of the plant may comprise pores, but it is generally recommended that an additional step of waxing is applied on the pores to protect the plant from harmful substances.

It should be recognized that a treatment area may span to various parts of a plant. For example, treatment area 404 may encompass the leaves, stems and the trunk of a plant. In another example, treatment area 404 may be limited to just one region or part of the plant (e.g., leaves, stems, bark, roots, etc.). Thus, it is contemplated that light energy may be applied to a first site and a second site on a plant that are different in kind (e.g., different tissues, cells, organs, systems of plant, distal).

It should be appreciated that the pores may vary in size and shape to account for differences in the absorption rate between various parts of the treatment area (e.g., the bark and the cuticle). For example, if it is determined that nucleic acids on a pore on the bark are absorbed slower than nucleic acids on a pore on the cuticle, then the pore on the bark may be larger to compensate for the slower absorption rate. Moreover, pores may be created to promote capillary action of the nucleic acids.

In another method, light energy may be used to create a first pore pattern. A first dosage of nucleic acid may be applied to the first pore pattern and a second dosage of nucleic acid may be applied to the first pore pattern after the first dosage is applied. For example, a first dosage of the first nucleic acid may be applied, then after a pre-determined time period, a second dosage of the first nucleic acid may be applied. In another example, a first dosage of the first nucleic acid may be applied, and then a first dosage of a second nucleic acid may be applied after a pre-determined time period.

The second nucleic acid may be any of the various nucleic acids described above. Additionally, the second substance may further include a booster or a catalyst for the first nucleic acid to further activate the first nucleic acid. It is contemplated that the second nucleic acid may produce a second biological response, wherein the second biological response may be connected to the first biological response or distinct from the first biological response. It is contemplated that the first and second dosage amounts are equal. In other embodiments, the first and second dosage amounts vary depending on the effective dosage amount required to produce a biological response.

Thus, it discovered that nucleic acids may be effectively delivered to a plant using light energy. The nucleic acids may be effective to interact with pathogens in the plant. However, it should be appreciated that effective delivery of nucleic acids may also interact with plant metabolism. Therefore, the delivery methods described herein may also be used to regulate genes within the plant. Due to the ability to modify genetic activity of the plant, nucleic acids applied to the plant may interact with nucleic acids that are normally found in the plant or with nucleic acids that are not normally found in a plant (e.g., transgenes). It is contemplated that nucleic acids may be delivered to a plant to activate or deactivate transgenes, which may include nucleic acids previously introduced into the plant.

Figure 5A:
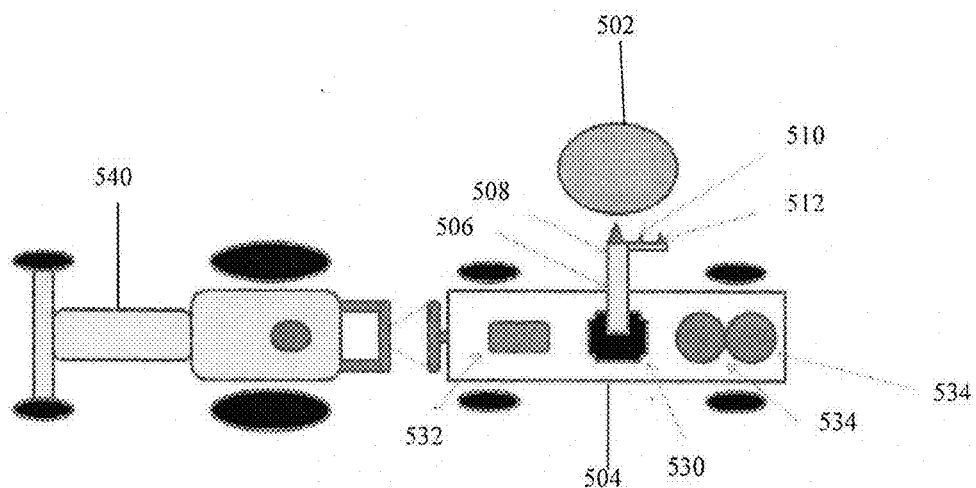
FIGS. 5A-5B is a top and perspective view of embodiments for delivering a nucleic acid to a plant.
Figure 5B:
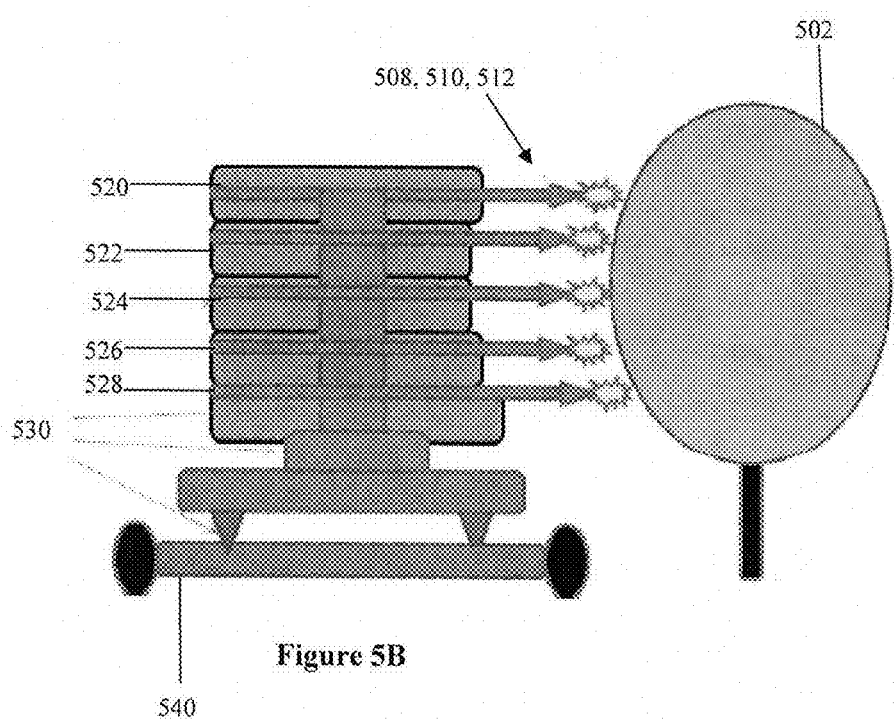

FIGS. 5A-5B show an embodiment of an apparatus 500 configured for delivering at least one nucleic acid to a plant 502. The apparatus may be mounted on a movable platform 504 for ease of use. The basic unit may comprise an electronically controlled robotic arm 506 containing: (i) a laser light emitter 508 to disperse a light to a treatment area or second site on a plant 502; (ii) a nucleic acid nozzle applicator 510; and (iii) a wax applicator 512 to seal the treated area as shown in FIG. 5A. The laser light emitter 508, nucleic acid nozzle applicator 510, and wax applicator 512 may be nozzles. All these nozzles may be mounted at the end of the arm on a movable bracket. In sequence, the laser light emitter 508 may emit light energy to create a momentary breach in the treatment area or second site on the plant 502, the nucleic acid nozzle applicator 510 may deliver the nucleic acid over the treatment area or second site on the plant 502, and the wax applicator 512 may reseal the treatment area or second site on the plant as the system moves forward. The system design may reduce the amount of substance needed by applying it only over the treatment area or second site on the plant, and not over the entire canopy/area and also ensures that the pores may be sealed to protect against water loss and other pathogens.

The apparatus 500 may further comprise five individual arms 520, 522, 524, 526, 528 as shown in FIG. 5B, each independently controlled and electronically actuated. These arms may be stacked vertically, with each laser having a scan window of approximately 14"×14". This will give a maximum laser treated height of approximately 6 ft. The design of the system may be modular so that more laser arms may be added vertically to accommodate larger trees if needed. The entire apparatus 500 may be mounted on the movable platform 504 which will be pulled through the grove by a tractor 540 at 2.3-2.7 mph. As the apparatus moves down the grove, optics will guide each arm to determined positions on the canopy, avoiding entanglement with branches of uneven length.

Each independently controlled arm 520, 522, 524, 526, 528, with the laser system and attached applicator nozzle assembly, may be designed to typically move in the horizontal direction. However, each laser system and assembly arm may move independently from the other arms. This independent scheme may allow each laser system to follow the contour of the tree canopy in its scan path. Multiple sensors on the articulating arm and laser system may ensure that it traces the tree canopy. The entire laser system may also be raised or lowered vertically depending on tree height. In addition, because of tree canopy irregularities and differing tree height, sensors on the laser may turn it "off and on" based on the presence of canopy to be treated within its scan path. The laser system and applicator nozzles may be attached on the arm using a rotating mount (not shown). This rotating mount may allow the lasers to be pointed at an angle to the tree canopy to better laser the adaxial (top) of the leaves.

In such a harsh working environment, the platform 504, on which the entire laser system is mounted on, may have an isolation design so that it will eliminate (as much as possible) the transfer of motion from the platform 504 to the apparatus 500 as it moves through the grove. The horizontal articulating robotic arms may also have isolation mounts 530 that are designed to minimize any further vibrations from affecting the operation of the laser system in the field. A generator 532 and tanks with pumps 534 may be mounted on the platform 504, as shown in FIG. 5A. The generator 532 provides sufficient power for the laser systems, pumps and associated electronic equipment. The tanks provide the storage for at least one of the substance and wax. The two pumps deliver the substance and wax to the applicator nozzles. The overall system design preferably takes into account environmental working conditions, heat, humidity, rain and varying grove conditions.

To the best of the inventor's knowledge, this is the first time RNAi has been introduced to the phloem after laser poration. Unexpectedly, the efficiency of RNAi was very high. Typically, at least 50%, 60%, 75%, 90%, and even 100% of all treatment areas resulted in a therapeutic response. Viewed from a different perspective, the inventor discovered that RNAi may be introduced into a plant by administering RNAi directly to the phloem through pores created by a laser.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of delivering at least one nucleic acid to a plant having an infected site, comprising:
   applying a light energy to a surface of the plant to create a pore;

applying at least one nucleic acid to the pore in an amount effective to induce a therapeutic response in the infected site; and wherein the infected site is in a phloem of the plant.

2. The method of claim 1, wherein the at least one nucleic acid comprises RNA.

3. The method of claim 2, wherein the at least one nucleic acid comprises at least one of a RNA interference (RNAi), an antisense RNA (asRNA), a micro RNA (miRNA), a small interfering RNA (siRNA), a double-stranded RNA (dsRNA), a non-coding RNA (ncRNA), mitochondrial RNA (mtDNA), and combinations thereof.

4. The method of claim 3, wherein the plant comprises a tree, a vine, a forage, a perennial crop, a row crop, a bush crop, an ornamental plant, an annual plant, or a grass.

5. The method of claim 1, wherein the at least one nucleic acid comprises DNA.

6. The method of claim 1, further comprising applying a second nucleic acid to the pore.

7. A method of modifying a plant having an infected site, comprising:

applying a light energy to a surface of the plant to create a pore;

applying at least one nucleic acid to the pore to allow uptake and delivery to the infected site; wherein the at least one nucleic acid is applied in an amount effective to produce a response; and wherein the infected site is in a phloem of the plant.

8. The method of claim 7, wherein the at least one nucleic acid comprises RNA.

9. The method of claim 8, wherein the at least one nucleic acid comprises at least one of an RNA interference (RNAi), an antisense RNA (asRNA), a micro RNA (miRNA), a small interfering RNA (siRNA), a double-stranded RNA (dsRNA), a non-coding RNA (ncRNA), mitochondrial RNA, and combinations thereof.

10. The method of claim 9, wherein the plant comprises a tree, a vine, a forage, a perennial crop, a row crop, a bush crop, an ornamental plant, an annual plant, or a grass.

11. The method of claim 7, wherein the at least one nucleic acid comprises DNA.

12. The method of claim 7, further comprising applying a second nucleic acid to the pore.

13. The method of claim 7, wherein the response comprises at least one of (i) modifying a gene expression to increase resistance to a pathogen in the plant, (ii) suppressing a virus-based vector in the plant, and (iii) modifying a gene expression to obtain a favorable trait in the plant.

14. A method of delivering at least one nucleic acid to a plant having an infected site, comprising:

applying a light energy to a treatment area on the plant to create a pore;

applying at least one nucleic acid to the pore in an amount effective to reduce a symptom of a pathogen in the infected site; and wherein the infected site is in a phloem of the plant.

15. The method of claim 14, wherein the applying a light energy and the applying a first dosage is within a predetermined time.

16. The method of claim 14, wherein the treatment area is a surface of at least one of a leaf, a stem, and a bark.

17. The method of claim 14, wherein the applying a light energy further comprises creating a second pore.

18. The method of claim 14, wherein the at least one nucleic acid comprises RNA.

19. The method of claim 18, wherein the at least one nucleic acid comprises at least one of a RNA interference (RNAi), an antisense RNA (asRNA), a micro RNA (miRNA), a small interfering RNA (siRNA), a double-stranded RNA (dsRNA), a non-coding RNA (ncRNA), mitochondrial RNA (mtDNA), and combinations thereof.

20. The method of claim 19, wherein the plant comprises a tree, a vine, a forage, a perennial crop, a row crop, a bush crop, an ornamental plant, an annual plant, or a grass.

21. The method of claim 14, wherein the at least one nucleic acid comprises DNA.

* * * * *